United States Patent [19]

Shirokov et al.

[11] 4,257,794
[45] Mar. 24, 1981

[54] METHOD OF AND APPARATUS FOR SEPARATING A GASEOUS HYDROCARBON MIXTURE

[76] Inventors: Vasily I. Shirokov, ulitsa S. Kovalevskoi, 10/4, kv. 105, Leningrad; Gennady G. Maljutin, ulitsa Kirova, 4, kv. 2, Novopolotsk; Ilyasaf I. Mishiev, 19 kvartal, 11, kv. 1, Sumgait; Nikolai N. Koshkin, Oktyabrskaya naberezhnaya, 100, korpus 3, kv. 11, Leningrad; Farida S. Abdullaeva, Vitebsky prospekt, 55, kv. 141, Leningrad; Anatoly K. Stukalenko, Grazhdanskaya ulitsa, 27, kv. 21, Leningrad; Alexandr N. Novichkov, ulitsa Sedova, 59, kv. 37, Leningrad; Jury V. Saveliev, ulitsa Pionerskaya, 18, kv. 10, Baku, all of U.S.S.R.

[21] Appl. No.: 59,381

[22] Filed: Jul. 20, 1979

[51] Int. Cl.³ .................................... F25J 3/02
[52] U.S. Cl. .............................. 62/28; 62/5; 62/23; 62/44
[58] Field of Search .......................... 62/23–28, 62/5, 42, 44

[56] References Cited

U.S. PATENT DOCUMENTS

| | | | |
|---|---|---|---|
| 3,443,388 | 5/1969 | Kramer et al. | 62/28 |
| 3,508,413 | 4/1970 | Pryor | 62/28 |
| 3,775,988 | 12/1973 | Fekete | 62/23 |

*Primary Examiner*—Norman Yudkoff
*Attorney, Agent, or Firm*—Steinberg & Raskin

[57] ABSTRACT

A method of separating a gaseous hydrocarbon mixture residing in cooling same by stages, with the resulting liquid condensate composed of the olefins and methane with an admixture of hydrogen being withdrawn at each cooling stage, recovering a gaseous methane-hydrogen mixture with some admixed ethylene produced by demethanization in a demethanizer, and further cooling same, withdrawing the resulting liquid condensate adapted for use as a spraying means in the process of demethanization. Expanding the remaining gaseous methane-hydrogen mixture with the application of the vortex effect providing thereby a hot gasiform stream and a cold gasiform stream. Mixing said hot and cold gasiform streams and again expanding the resulting mixture with the application of vortex effect. Feeding the hot stream produced thereby countercurrently against the gaseous hydrocarbon mixture being separated, and a cold stream—upon having it previously having passed countercurrently against the gasiform methane-hydrogen ethylene mixture. An apparatus for implementing this method comprises a unit adapted for recovering the olefins and incorporating tubular heat exchangers associated with one another in series, coolers and separators, and a unit adapted for recovering a gasiform methane-hydrogen mixture with an admixture of ethylene and incorporating a demethanizer, a tubular condenser, a separator, and first and second vortex tubes, all of which are associated with one another. The liquid-containing sections of all of the separators of the unit for recovery of the olefins are associated with the demethanizer. The second vortex tube has its nozzle inlet associated directly with the hot end of the first vortex tube, and with its cold end—via a portion of the tubes of the tubular condenser. The second vortex tube has its hot end associated with the tubes of the tubular heat exchangers of the unit for recovery of the olefins, and its cold end—via the rest of the tubes of the tubular condenser.

2 Claims, 1 Drawing Figure

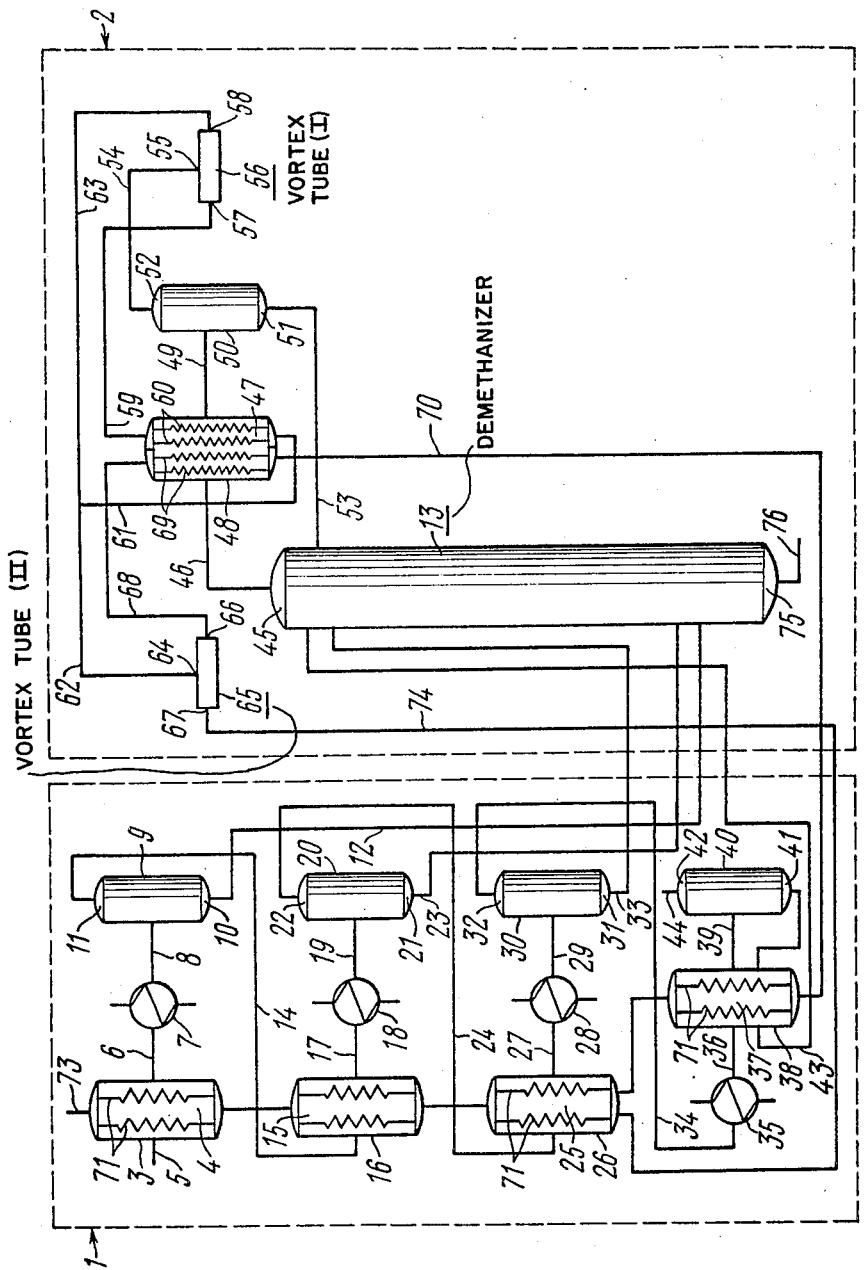

METHOD OF AND APPARATUS FOR SEPARATING A GASEOUS HYDROCARBON MIXTURE

FIELD OF THE INVENTION

The present invention relates generally to the field of petroleum refining, and more specifically, to methods of and apparatus for separating gaseous hydrocarbon mixtures.

The invention can be used most advantageously in separating a gaseous methane-hydrogen mixture from olefins (ethylene, ethane, propylene, propane, a $C_4$ fraction admixture) in the processes of production of high-purity ethylene and propylene available from gaseous hydrocarbon mixtures including essentially hydrogen, methane and olefins.

BACKGROUND OF THE INVENTION

Ethylene and propylene have found the most extensive application in present-day petroleum refining processes, which are employed in the production of numerous plastic materials, e.g. polyethylene, polypropylene, copolymers of ethylene and propylene, etc. Such processes are known to involve fairly rigorous requirements for ethylene and propylene purities, for example, the methane content in ethylene should not exceed $0.0005+0.001$ mole percent. Hence, it is quite evident that the production of ethylene of such a high purity degree in the separation of gaseous hydrocarbon mixtures calls for the heaviest expenditure of energy precisely in the process of isolating methane from olefins.

The major raw material currently consumed by the petroleum refining industry in all of the technologically advanced countries is ethylene, the annual output of which has reached up to 35-40 mln.t.

Thus, provision of economic and highly efficient methods of and apparatus for separating gaseous hydrocarbon mixtures becomes a vitally urgent problem.

The prior state of the art has utilized quite a variety of methods and apparatus for separating gaseous hydrocarbon mixtures and, in particular, for separating a methane-hydrogen fraction from olefins.

Specifically, in the prior art there is known a method for recovery of the olefins and methane and hydrogen from a gaseous mixture of hydrocarbon compounds including primarily hydrogen, methane and olefins (cf. U.S. Pat. No. 3,443,388). According to this method the gaseous mixture is cooled in a plurality of stages of successively lower temperatures to effect condensation of most of the gas comprised essentially of the olefins and a portion of methane with traces of hydrogen. The condensate withdrawn from each stage of cooling is passed for introduction into a demethanizer, from the top of which a gasiform methane-hydrogen mixture with traces of ethylene is removed, while from the bottom thereof the olefins are removed and passed for further separation. The gasiform methane-hydrogen mixture with traces of ethylene is subjected to cooling to produce a gas-liquid mixture. The resulting gas-liquid mixture is divided into gaseous and liquid portions. The gaseous portion consisting of the methane-hydrogen mixture with traces of ethylene is withdrawn, and the liquid methane-ethylene portion is divided into two streams, with one of said streams being fed into the demethanizer by a means of spraying, while the other one is vaporized at a low pressure. The amounts of refrigeration obtained thereby are used for the aforesaid cooling of the gasiform methane-hydrogen mixture with traces of ethylene.

The method described above is incorporated in an apparatus comprising a unit for recovery of the olefins and a portion of methane with traces of hydrogen and a unit for recovery of a gasiform methane-hydrogen mixture with traces of ethylene. The unit for recovery of the olefins consists of coolers associated with one another in series and providing the cooling of the gaseous mixture under separation, in stages and separators providing the separation of the resulting gas-liquid mixtures into a gaseous stream and a liquid stream. The unit for recovery of a gasiform methane-hydrogen mixture with traces of ethylene consists of a demethanizer, a tubular condenser, a separator and a throttle valve. The demethanizer is associated with the liquid-containing sections of the separators of the unit for recovery of the olefins. The top of the demethanizer is associated with the separator via the intertubular space of the tubular condenser. The gas-containing section of the separator is associated with a bleeding pipe. The liquid-containing section of the separator is associated directly with the top of the demethanizer and with the tubes of the condenser via the throttle valve. The tubes of the condenser are in turn associated with the bleeding pipe.

A disadvantage of the foregoing method and apparatus for separating gaseous hydrocarbon mixtures consists in that a portion of the liquid comprised of methane with traces of ethylene is employed in order to secure refrigeration in the unit for recovery for a gasiform methane-hydrogen mixture with traces of ethylene, which results in ethylene losses. The level of temperatures obtained thereby fails to afford complete condensation of ethylene from the gasiform methane-hydrogen mixture being withdrawn, which also results in ethylene losses.

Furthermore, the foregoing method and apparatus do not take full advantage of the energy potentialities of the compressed gasiform methane-hydrogen mixture with traces of ethylene being withdrawn in order to gain additional amounts of refrigeration.

In the prior art there is also known a method and apparatus for separating a gaseous hydrocarbon mixture including essentially hydrogen, methane and olefins (see U.S. Journal "Chemical Engineering Progress," 1971, V. 67, No. 2, pp. 41–44), which partially eliminate the disadvantages inherent in the above method and apparatus. According to this method the gaseous mixture is cooled in a plurality of stages of sequentially lower temperatures to accomplish condensation of a major portion of the gas comprised primarily of the olefins and a portion of methane with traces of hydrogen. The condensate withdrawn from each stage of cooling is fed into a demethanizer, the top of which is adapted for removal of a gasiform methane-hydrogen mixture with traces of ethylene, while the bottom thereof is adapted for removal of the olefins which are passed then for further separation.

The gasiform methane-hydrogen mixture with traces of ethylene is subjected to cooling by amounts of cold generated in the process of ethylene boiling. As a result, a gas-liquid mixture is produced, which is further separated into a gaseous portion and a liquid portion. The liquid portion comprised of methane and ethylene is fed into a demethanizer as a spraying means. The gaseous portion of the methane-hydrogen mixture with traces of ethylene is subjected to further cooling to produce a gas-liquid mixture. The resulting gas-liquid mixture is divided into a gaseous portion and a liquid portion. The liquid portion comprised of methane with traces of ethylene is fed into the demethanizer as a spraying means. The gaseous portion of the methane-hydrogen mixture with traces of ethylene is throttled to a low pressure and removed. The amounts of refrigeration obtained thereby are used for said cooling of the methane-hydrogen mixture with traces of ethylene.

The method described above is incorporated in an apparatus comprising a unit for recovery of the olefins and a portion of methane with traces of hydrogen, and a unit for recovery of a gasiform methane-hydrogen mixture with traces of ethylene. The unit for recovery of the olefins consists of coolers associated therebetween in series and providing the cooling of the gaseous mixture being separated in stages, and separators providing the separation of the resulting gas-liquid mixtures produced thereby into a gaseous portion and a liquid portion. The unit for recovery of a gasiform methane-hydrogen mixture with traces of ethylene consists of a demethanizer, a cooler wherein liquid ethylene is used as a cooling agent, a separator, a tubular condenser, a further separator and a throttle valve. The demethanizer is associated with the liquid-containing sections of the separators of the unit for recovery of the olefins. The top of the demethanizer is associated with the separator via the cooler. The liquid-containing section of the separator is associated with the top of the demethanizer. The gas-containing section of the separator is associated with another separator via the intertubular space of the tubular condenser. The liquid-containing section of this separator is associated with the top of the demethanizer, while its gas-containing section is associated with the tubes of said condenser via the throttle valve. The tubes of the condenser are in turn associated with a bleeding pipe.

Although in this method the throttling of the compressed gasiform methane-hydrogen mixture being withdrawn is employed in order to secure additional refrigeration, still the throttling process does not take full advantage of the energy potentialities available in it. The level of temperatures provided thereby does not afford complete condensation of ethylene from the gasiform methane-hydrogen mixture being withdrawn, which results in loss of ethylene.

Moreover, the employment of liquid ethylene to secure the refrigeration required for the cooling of the gasiform mixture withdrawn from the demethanizer brings about an additional increase in the expenditure of energy.

In the petroleum refining industry there is generally known a method of separating gaseous hydrocarbon mixtures, which partially overcomes the disadvantages of the foregoing methods. According to this method the gaseous hydrocarbon mixture including essentially hydrogen, methane and olefins, is cooled by stages to temperatures ensuring removal of the olefins and a portion of the methane with an admixture of hydrogen therefrom in the form of a liquid condensate. The liquid condensate formed at each of these cooling stages is separated from the remaining gaseous mixture and passed for demethanization. The remainder of the gaseous mixture obtained at the last cooling stage, comprised of hydrogen, methane and an admixture of ethylene, is removed for the purpose of further recovering hydrogen therefrom. The gasiform methane-hydrogen mixture with an admixture of ethylene formed by demethanization of the liquid condensates is passed for further cooling. The resulting liquid condensate comprised of methane and ethylene is separated and used as a spraying means in the process of demethanization. The remaining gasiform portion of the methane-hydrogen mixture with an admixture of ethylene is subjected to expanding with the application of vortex effect, as a result of which a cold gasiform stream and a hot gasiform stream are produced. The hot stream is passed to the fuel network. The cold stream is used for the aforesaid cooling of the methane-hydrogen mixture with an admixture of ethylene, whereafter it is also passed to the fuel network.

The abovestated method is incorporated in an apparatus comprising a unit for recovery of the olefins and a portion of the methane with an admixture of hydrogen, a unit for recovery of a gasiform methane-hydrogen mixture with an admixture of ethylene. The unit for recovery of the olefins and a portion of the methane with an admixture of hydrogen consists of tubular heat exchangers and coolers, providing the cooling of the gaseous mixture being separated by stages, and separators having gas-containing and liquid-containing sections and intended for the separation of the gas-liquid mixtures formed at each cooling stage into a gaseous stream and a liquid stream.

The tubes of all the tubular heat exchangers are interconnected in series, while their intertubular spaces are interconnected via the coolers and the gas-containing sections of the separators. The unit for recovery of a gasiform methane-hydrogen mixture with an admixture of ethylene consists of a demethanizer having the liquid-containing sections of the separators of the unit for recovery of the olefins connected thereto, a tubular condenser providing the cooling of the gasiform methane-hydrogen mixture with an admixture of ethylene to form a gas-liquid mixture, a separator having a gas-containing section and a liquid-containing section and providing the separation of this mixture into a gaseous stream and a liquid stream, and a vortex tube intended for the expansion of the gaseous stream and having a nozzle inlet, a cold end and a hot end.

The top of the demethanizer is connected to the nozzle inlet of the vortex tube via the intertubular space of the tubular condenser and the gas-containing section of the separator. The liquid-containing section of the separator is connected to the top of the demethanizer. The cold end of the vortex tube is connected to the tubes of the tubular condenser, which in turn are connected to a bleeding pipe. The hot end of the vortex tube is also connected to the bleeding pipe.

The application of the vortex effect in order to secure the refrigeration necessary for the cooling of the gasiform methane-hydrogen mixture with an admixture of ethylene permits taking advantage of its energetic potentialities more fully as compared to the foregoing methods. However, the hot gasiform stream removed from the apparatus possesses considerable energy which is not employed to secure additional refrigeration in this method and apparatus. The level of temperatures obtained therewith fails to afford complete condensation of ethylene from the gasiform methane-hydrogen mixture being withdrawn, which results in loss of ethylene.

It should be noted that all the methods and apparatus described above do not enable to recover ethylene from the gasiform methane-hydrogen mixture completely and the degree of ethylene recovery does not exceed 98%.

SUMMARY OF THE INVENTION

The present invention directed at avoiding or minimizing the aforesaid disadvantages.

It is an object of the present invention to provide a method of and apparatus for separating olefins from a gaseous hydrocarbon mixture to take full advantage of the energy potential of the gasiform methane-hydrogen mixture being withdrawn as a residue.

Another object of the present invention is to reduce the losses of ethylene from the gasiform methane-hydrogen mixture being withdrawn.

With these and other objects in view, the present invention resides in a method of separating a gaseous hydrocarbon mixture including essentially hydrogen, methane and olefins, comprising cooling said gaseous mixture by stages to temperature levels sufficient to provide removal of the olefins and a portion of the methane with an admixture of hydrogen therefrom in the form of a liquid condensate, with same being withdrawn from this mixture at each cooling stage and being fed for demethanization to a demethanizer, recovering a gasiform methane-hydrogen mixture with an admixture of ethylene traces, produced by demethanization of the liquid condensate, further cooling same, with a liquid condensate produced thereby being withdrawn and used as a spraying means in the process of demethanization, expanding the remaining gasiform portion of the methane-hydrogen mixture by an admixture of ethylene with the application of the vortex effect, providing thereby a cold gasiform stream and a hot gasiform stream, said cold stream being employed for the purpose of the cooling of the gasiform methane-hydrogen mixture with an admixture of ethylene, wherein, according to the invention, the cold gasiform stream, upon its having been employed for the purpose of the cooling the gasiform methane-hydrogen mixture with an admixture of ethylene, is mixed by hot gasiform stream and expanded with the application of the vortex effect to produce thereby a cold gasiform stream and a hot gasiform stream, whereafter the hot stream is directly fed in a countercurrent manner against the gaseous mixture being separated, and the cold stream—upon having it previously passed in a countercurrent manner against the gasiform methane-hydrogen mixture with an admixture of ethylene traces produced by demethanization.

With the foregoing objects in view, the invention also resides in an apparatus for separating a gaseous hydrocarbon mixture, comprising a unit for recovery of the olefins from the gaseous mixture being separated, incorporating tubular heat exchangers and coolers providing the cooling of said gaseous mixture by stages, and separators having a gas-containing section and a liquid-containing section, both providing the separation of the gas-liquid mixtures being produced at each cooling stage into a gaseous stream and a liquid stream, with the tubes of all the tubular heat exchangers being associated therebetween in series, and their intertubular spaces being associated therebetween via the coolers and the gas-containing sections of the separators, a unit for recovery of a gasiform methane-hydrogen mixture with an admixture of ethylene, incorporating a demethanizer having the liquid-containing sections of the separators of the unit for recovery of the olefins associated therewith, a tubular condenser providing the cooling of the gasiform methane-hydrogen mixture with an admixture of ethylene, a separator providing the separation of the gas-liquid mixture produced thereby into a gaseous stream and a liquid stream and having a gas-containing section, and a liquid-containing section associated with the top of the demethanizer, a vortex tube for the expansion of the gasiform methane-hydrogen mixture resulting in the formation of a cold gasiform stream and a hot gasiform stream and having a nozzle inlet associated with the top of the demethanizer via the gas-containing section of the separator and the intertubular space of the tubular condenser, a cold end associated with the tubes of the tubular condenser, intended for the passage of the cold stream being discharged therefrom, and a hot end, wherein, according to the invention, the unit for recovery of a gasiform methane-hydrogen mixture with an admixture of ethylene traces incorporates an additional vortex tube having a nozzle inlet associated directly with the hot end of said first vortex tube and associated with its cold end via the tubes of the tubular condenser associated therewith, a cold end and a hot end, with the hot end being associated directly with the tubes of the tubular heat exchangers of the unit for recovery of the olefins, and the cold end—via the tubes of the tubular condenser intended for the passage of the cold stream being discharged therefrom.

The proposed apparatus permits taking full advantage of the energetic potentialities available in the compressed gasiform methane-hydrogen mixture being withdrawn in order to gain additional amounts of refrigeration. The level of temperatures obtained thereby within $-145°$ to $150°$ C. permits minimizing the losses of ethylene. The degree of ethylene recovery amounts to 99% and higher. No supplementary energy sources to provide refrigeration are required.

The abovementioned and other objects as well as the advantages of the proposed invention will become more readily apparent on consideration of the detailed description of an embodiment thereof with reference being made to the accompanying drawing, in which there is illustrated a basic process flow diagram.

DETAILED DESCRIPTION OF THE INVENTION

The proposed method of separating a gaseous hydrocarbon mixture including essentially hydrogen, methane and olefins, resides in cooling said mixture in a number of stages to sequentially lower temperatures to effect condensation of a major portion of the gas comprised of the higher boiling components, with the temperature of the last cooling stage being selected so that the gas withdrawn therefrom has the lowest boiling point.

The gaseous mixture being separated is cooled by stages to temperature levels sufficient to provide removal of the olefins, and contains a portion of the methane with an admixture of some hydrogen therefrom, in the form of a liquid condensate. The resulting liquid condensate formed at each cooling stage is separated from the remainder of the gaseous mixture and passed to a demethanizer for demethanization. The remainder of the gaseous mixture including essentially hydrogen and methane with an admixture of small amounts of the olefins and produced after removal of the major portion of olefins, is withdrawn for the purpose of further recovering hydrogen therefrom (this part of the process is not considered in the present invention). The gasiform methane-hydrogen mixture with an admixture of some of the ethylene produced by demethanization of the liquid condensates is passed for further cooling, with a liquid condensate, comprised of methane and ethylene and produced thereby being withdrawn and is used as a spraying means in the demethanizer in the process of demethanization. The remaining gasiform portion of the methane-hydrogen ethylene-contaminated mixture is expanded by the application of the vortex effect, as a result of which a cold gasiform stream and a hot gasiform stream are produced.

The cold stream is employed for the cooling of said gasiform methane-hydrogen ethylene mixture being formed, whereafter the cold stream is mixed by the hot stream and expanded with the application of the vortex effect, as a result of which a cold stream and a hot stream are produced. The hot stream is directly fed in a countercurrent manner against the gaseous hydrocarbon mixture being separated, while the cold stream—upon having it previously passed in a countercurrent manner against said gasiform methane-hydrogen ethylene mixture being produced by demethanization.

The proposed apparatus for practising this method of separating a gaseous hydrocarbon mixture including essentially hydrogen, methane and olefins, comprises a unit 1 for recovery of the olefins and a unit 2 for recovery of a gasiform methane-hydrogen mixture contaminated with ethylene. The unit 1 for recovery of the olefins from the gaseous mixture being separated incorporates a tubular heat exchanger 3, the intertubular space 4 of which is associated via a pipeline 5 with a source of the starting gaseous mixture (not shown in the drawing), and via a pipeline 6 with a cooler 7. The cooler 7 is in turn associated with a separator 9 via a pipeline 8, which separator is provided with a liquid-containing section 10 and a gas-containing section 11. The liquid-containing section 10 of the separator 9 is associated via a pipeline 12 with a demethanizer 13 of the unit 2 for recovery of the gasiform methane-hydrogen mixture. The gas-containing section 11 of the separator 9 is associated via a pipeline 14 with the intertubular space 15 of a tubular heat exchanger 16. Its intertubular space 15 is associated via a pipeline 17 with a cooler 18, which in turn is associated via a pipeline 19 with a separator 20 having a liquid-containing section 21 and a gas-containing section 22. The liquid-containing section 21 of the separator 20 is associated via a pipeline 23 with the demethanizer 13. The gas-containing section 22 of the separator 20 is associated via a pipeline 24 with the intertubular space 25 of a tubular heat exchanger 26. Its intertubular space 25 is associated via a pipeline 27 with a cooler 28 which in turn is associated via a pipeline 29 with a separator 30 having a liquid-containing section 31 and a gas-containing section 32. The liquid-containing section 31 of the separator 30 is associated via a pipeline 33 with the demethanizer 13. The gas-containing section 32 of the separator 30 is associated via a pipeline 34 with a cooler 35, which in turn is associated via a pipeline 36 with the intertubular space 37 of a tubular heat exchanger 38. Its intertubular space 37 is associated via a pipeline 39 with a separator 40 having a liquid-containing section 41 and a gas-containing section 42. The liquid-containing section 41 of the separator 40 is associated via a pipeline 43 through the intertubular space 37 of the tubular heat exchanger 38 with the demethanizer 13. The gas-containing section 42 of the separator 40 is associated with a pipeline 44 intended for the withdrawal of the gasiform mixture including essentially hydrogen and methane with an admixture of some of the olefins from the apparatus. The unit 2 for recovery of a gasiform methane-hydrogen mixture with an admixture of contaminating ethylene incorporates the demethanizer 13 having its top 45 associated via a pipeline 46 with the intertubular space 47 of a tubular condenser 48. Its intertubular space 47 is associated primarily via a pipeline 49 with a separator 50 having a liquid-containing section 51 and a gas-containing section 52. The liquid-containing section 51 of the separator 50 is associated via a pipeline 53 with the top 45 of the demethanizer 13. The gas-containing section 52 of the separator 50 is associated via a pipeline 54 with the nozzle inlet 55 of a vortex tube 56 having a cold end 57 and a hot end 58. The cold end 57 of the vortex tube 56 is associated via a pipeline 59 with the tubes 60 of the tubular condenser 48. The tubes 60 are associated via a pipeline 61 with a pipeline 62. The hot end 58 of the vortex tube 56 is also associated via a pipeline 63 with the pipeline 62. The pipeline 62 is associated with the nozzle inlet 64 of a vortex tube 65 having a cold end 66 and a hot end 67. The cold end 66 of the vortex tube 65 is associated via a pipeline 68 with tubes 69 of the tubular ccondenser 48. The tubes 69 are associated via a pipeline 70 with the tubes 71 of the tubular heat exchangers 38, 26, 16 and 3, which are associated therebetween via a pipeline 72. The tubes 71 of the tubular heat exchanger 3 are associated with a pipeline 73 intended for the withdrawal of the gasiform methane-hydrogen mixture from the apparatus. The hot end 67 of the vortex tube 65 is associated via a pipeline 74 with the tubes 71 of the heat exchanger 26. The bottom 75 of the demethanizer 13 is associated with a pipeline 76 adapted for the withdrawal of the olefins from the apparatus.

A process for separating a gaseous hydrocarbon mixture according to the flow diagram of the FIGURE of the present invention will now be considered.

The starting gaseous mixture including essentially hydrogen, methane and olefins (ethylene, ethane, propylene, propane, a $C_4$ fraction admixture) at a pressure of 32–38 mn/m$^2$ and a temperature of $+15°$ C. is passed through the pipeline 5 into the intertubular space 4 of the tubular heat exchanger 3 of the unit 1 for recovery of the olefins from the gaseous mixture being separated. This gaseous mixture is cooled in the heat exchanger 3 by the products of its separation (a gasiform methane-hydrogen mixture) to a temperature of $-5°$ to $-10°$ C. and is passed then via the pipeline 6 into the cooler 7 being cooled by liquid propylene, which is vaporized at a temperature of $-18°$ C. Said gaseous mixture is cooled in the cooler 7 to a temperature of $-15°$ C., as a result of which a major portion of the $C_4$ fraction, propylene, propane and a portion of ethane and ethylene are condensed. The resulting gas-liquid mixture is passed via the pipeline 8 into the separator 9, wherein it is separated into a liquid condensate and a remainder of the gaseous mixture. The liquid condensate from the liquid-containing section 10 of the separator 9 is passed via the pipeline 12 into the demethanizer 13, while the remainder of the gaseous mixture from the gas-containing section 11 of this separator is passed via the pipeline 14 for further cooling in the intertubular space 15 of the tubular heat exchanger 16 being cooled by the products of the separation of the gaseous mixture. The gaseous mixture is cooled in the heat exchanger 16 to a temperature of $-20°$ to $-25°$ C. and passed then via the pipeline 17 into the cooler 18, being cooled by liquid propylene which is vaporized at a temperature of $-37°$ C.

Said gaseous mixture is cooled in the cooler 18 to a temperature of −30° to −35° C., as a result of which the C$_4$ fraction, propylene, propane are condensed completely, and a major portion of ethane and ethylene and a portion of methane and hydrogen are also condensed. The resulting gas-liquid mixture is passed via the pipeline 19 into the separator 20, wherein it is separated into a liquid condensate and a remainder of the gaseous mixture. The liquid condensate from the liquid-containing section 21 of the separator 20 is passed through the pipeline 23 into the demethanizer 13, while the remainder of the gaseous mixture from the gas-containing section 22 of this separator is passed through the pipeline 24 for further cooling in the intertubular space 25 of the tubular heat exchanger 26 being cooled by the products of the separation of the gaseous mixture. The gaseous mixture is cooled in the heat exchanger 26 to a temperature of −35° to −40° C. and passed then through the pipeline 27 into the cooler 28 being cooled by liquid ethylene which is vaporized at a temperature of −36° C. The gaseous mixture is cooled in the cooler 28 to a temperature of −50° to −53° C., as a result of which a major portion of ethylene and ethane and a portion of methane and hydrogen are condensed. The resulting gas-liquid mixture is passed through the pipeline 29 into the separator 30 wherein it is separated into a liquid condensate and a remainder of the gaseous mixture. The liquid condensate from the liquid-containing section 31 of the separator 30 is passed through the pipeline 33 into the demethanizer 13, while the remainder of the gaseous mixture from the gas-containing section 32 of this separator is passed via the pipeline 34 into the cooler 35 being cooled by liquid ethylene which is vaporized at a temperature of −98° C. The gaseous mixture is cooled in the cooler 35 to a temperature of −92° to −95° C. and passed then via the pipeline 36 into the intertubular space 37 of the tubular heat exchanger 38 being cooled by the products of the separation of the gaseous mixture. The gaseous mixture is cooled in the heat exchanger 38 to a temperature of −100° C., as a result of which almost all of ethylene and ethane, a substantial portion of methane and a portion of hydrogen are condensed. The resulting gas-liquid mixture is passed via the pipeline 39 into the separator 40, wherein it is separated into a liquid condensate and a remainder of the gaseous mixture including hydrogen and methane with an admixture of some ethylene and ethane. The liquid condensate from the liquid-containing section 41 of the separator 40 is passed via the pipeline 43 through the intertubular space 37 of the tubular heat exchanger 38 into the demethanizer 13. The remainder of the gaseous mixture from the gas-containing section 42 of the separator 40 is withdrawn via the pipeline 44 from the apparatus for the purpose of further recovering hydrogen therefrom.

The gasiform methane-hydrogen mixture with an admixture of ethylene is separated in the demethanizer 13 from the liquid condensates passed thereto via the pipelines 12, 23, 33 and 43, and said gaseous mixture is then withdrawn from the top 45 of the demethanizer 13 through the pipeline 46. The liquid olefins are withdrawn from the bottom 75 of the demethanizer through the pipeline 76. The said gasiform methane-hydrogen mixture with an admixture of ethylene traces is passed via the pipeline 46 at −95° to 100° C. into the intertubular space 47 of the tubular condenser 48 being cooled by the products of the separation of the gaseous mixture. This gaseous mixture is cooled in the condenser 48 to a temperature of −135° to −140° C., as a result of which almost all of ethylene, a portion of methane and an insignificant portion of hydrogen are condensed. The resulting gas-liquid mixture is passed via the pipeline 49 into the separator 50 wherein it is separated into a liquid condensate and a remainder of the gasiform methane-hydrogen mixture. The liquid condensate from the liquid-containing section 51 of the separator 50 is passed via the pipeline 53 into the demethanizer 13 as a spraying means. The remainder of the gasiform methane-hydrogen mixture from the gas-containing section 52 of the separator 50 is passed via the pipeline 54 for expansion in the vortex tube 56 through its nozzle inlet 55. As a result of expansion in the vortex tube 56 from a pressure of 32 to 38 mn/m$^2$ to a pressure of 15 to 18 mn/m$^2$ said gaseous mixture is separated into two streams, a cold stream having a temperature of −145° to −150° C., and a hot stream having a temperature of −105° to −110° C. The cold stream is discharged from the vortex tube 56 through its cold end 57 and is passed via the pipeline 59 into the tubes 60 of the tubular condenser 48. When passing through these tubes countercurrently against the gasiform methane-hydrogen mixture containing some ethylene the cold stream is heated to a temperature of −105° to −110° C. and passed via the pipeline 61 into the pipeline 62. The hot stream is discharged from the vortex tube 56 through its hot end 58 and is also passed via the pipeline 63 into the pipe line 62. The hot and cold streams are mixed in the pipeline 62 and are passed for expansion into the vortex tube 65 through its nozzle inlet 64. As a result of expansion in the vortex tube 65 from a pressure of 15 to 18 mn/m$^2$ to a pressure of 2.5 to 3.5 mn/m$^2$ the gaseous mixture is separated into two streams,—a cold stream having a temperature of −145° to −150° C., and a hot stream having a temperature of −95° to −100° C. The cold stream is discharged from the vortex tube 65 through its cold end 66 and passed via the pipeline 68 into the tubes 69 of the tubular condenser 48. When passing through these tubes countercurrently against the gasiform methane-hydrogen mixture with ethylene traces the cold stream is heated to a temperature of −105° to −110° C. and further passed via the pipeline 70 into the tubes 71 of the tubular heat exchanger 38. When passing through these tubes countercurrently against the gaseous mixture being separated, the cold stream is heated to a temperature of −95° to −100° C. and passed via the pipeline 72 into the tubes 71 of the tubular heat exchanger 26. The hot stream is discharged from the vortex tube 65 through its hot end 67 and passed via the pipeline 74 into said tubes 71 of the tubular heat exchanger 26. The hot and cold streams are mixed and this methane-hydrogen mixture is further passed through the tubes 71 of the tubular heat exchangers 26, 16 and 3 in a countercurrent manner against the gaseous mixture being separated, as a result of which the methane-hydrogen is heated to a temperature of −10° to 15° C. and is withdrawn from the apparatus via the pipeline 73.

In order to make the invention more clearly understood an example of the specific embodiment thereof in accordance with the above described process flow diagram is given below.

EXAMPLE

To produce the starting gaseous mixture gasoline boiling between 62° to 180° C. is subjected to pyrolysis at a temperature of 823° to 850° C. with an addition of vapor constituting 50 percent by weight of the gasoline bulk. The resulting pyrogas is cooled to a temperature of 20° to 30° C. and compressed from a pressure of 1.2 to 1.3 mn/m² to a pressure of 30 to 40 mn/m², with acid gases being removed from the gaseous mixture. Heavy C₄ and higher hydrocarbons are removed from the gaseous mixture, and the remaining gaseous mixture is hydrogenated to remove acetylenic compounds, dehumidified and cooled to a temperature of +15° C.

The resulting gaseous mixture comprised of hydrogen, methane and the remaining olefins is treated in accordance with the process flow diagram as specified hereinabove.

A material balance of the streams conveyed through the respective pipelines of the mentioned process flow diagram is given in the appended table.

The table given below is illustrative of the specific operating conditions for an embodiment of the method of the present invention, but it is to be clearly understood that the scope of the present invention is not to be limited thereby.

From the specific embodiment of the present invention it becomes readily apparent for those skilled in the art that all the objects of the invention within the scope defined by the appended claims are achievable. However, it is also apparent that some modifications and variations in the performance of the steps of the method of separating a gaseous hydrocarbon mixture as well as in the structure of the apparatus for practising this method are possible without departing from the spirit of the invention.

All such specifications and variations are considered to be well within the spirit and scope of the invention defined by the appended claims.

The proposed method of and apparatus for separating a gaseous hydrocarbon mixture are highly efficient. According to the method of the present invention the losses of ethylene with the gasiform methane-hydrogen mixture being withdrawn from the apparatus are actually absent. The degree of ethylene recovery amounts to 99% and higher. The temperatures within from −145° to −150° C., which secure such a high degree of ethylene recovery, are attained merely at the expense of taking full advantage of the energy potential available in the pressurized gasiform methane-hydrogen mixture. No additional energy sources are required. At the same time the total energy demand is cut down to 15% and more.

The apparatus for practising the method is quite simple in design because of the complete absence of the structural elements requiring moving parts. The apparatus is reliable in operation and is readily automated.

TABLE

A material balance of the streams conveyed through the respective pipelines of the process flow diagram of the invention

| STREAM No. | COMPONENT | 5 wt % | 12 wt % | 23 wt % | 33 wt % | 43 wt % | 44 wt % | 46 wt % | 53 wt % | 59 wt % | 63 wt % | 68 wt % | 74 wt % | 75 wt % |
|---|---|---|---|---|---|---|---|---|---|---|---|---|---|---|
| 1 | Hydrogen | 1.72 | 0.065 | 0.08 | 0.11 | 0.18 | 11.62 | 1.48 | 2.0 | 5.71 | 0.06 | 5.3 | 0.12 | — |
| 2 | Methane | 23.95 | 5.48 | 8.08 | 12.51 | 31.13 | 78.63 | 95.63 | 82.62 | 94.29 | 99.71 | 94.7 | 99.58 | 0.001 |
| 3 | Ethylene | 38.69 | 28.45 | 38.03 | 50.11 | 54.04 | 7.03 | 2.88 | 14.72 | — | 0.28 | — | 0.30 | 52.029 |
| 4 | Ethane | 9.82 | 9.75 | 11.85 | 18.50 | 9.38 | 1.58 | 0.01 | 0.66 | — | — | — | — | 18.23 |
| 5 | Propylene | 24.47 | 52.91 | 39.98 | 22.87 | 4.56 | 1.14 | — | — | — | — | — | — | 27.96 |
| 6 | Propane | 1.04 | 2.47 | 1.60 | 0.84 | 0.45 | — | — | — | — | — | — | — | 1.40 |
| 7 | C₄ fraction | 0.31 | 0.865 | 0.38 | 0.06 | 0.26 | — | — | — | — | — | — | — | 0.38 |
| | Total | 100.0 | 100.0 | 100.0 | 100.0 | 100.0 | 100.0 | 100.0 | 100.0 | 100.0 | 100.0 | 100.0 | 100.0 | 100.0 |
| | Temperature °C., | +15 | −15 | −30 | −50 | −100 | −100 | −100 | −125 | −150 | −108 | −150 | −105 | +10 |
| | Pressure, kg/cm² | 38.0 | 37.9 | 37.7 | 37.6 | 37.4 | 37.4 | 37.0 | 37.0 | 18.0 | 18.0 | 3.5 | 3.5 | 36.8 |

What is claimed is:

1. A process for separating the olefins from a pressurized gaseous hydrocarbon feed mixture including essentially hydrogen, methane and olefins which comprise the steps of:

cooling said hydrocarbon mixture by sequential stages to temperature levels to form a liquid condensate of the olefins, and a portion of the methane with some hydrogen;

separating at each cooling stage, the liquid condensate from the gaseous residue;

demethanizing the liquid condensate from each cooling stage to separate the pure olefins from the formed residual gaseous mixture of hydrogen, methane and ethylene traces;

cooling the gaseous hydrogen-methane-ethylene mixture from demethanization;

separating a liquid condensate from said cooled mixture for use as a spray in the demethanization step;

introducing the cooled gaseous residue from the cooled hydrogen-methane-ethylene mixture into a first vortex effect tube to form upon expansion therein a hot gaseous steam and a cold gaseous stream;

cooling, with said cold stream, the gaseous hydrogen-methane-ethylene mixture from the demethanization step;

mixing said hot and cold gas streams to form a gaseous mixture;

introducing said gaseous mixture into a second vortex effect tube to form a further cold gaseous stream and a further hot gaseous stream;

introducing said further hot gaseous stream in counter-current heat exchange relationship to said gaseous hydrocarbon feed;

cooling with said further cold stream first the hydrogen-methane-ethylene mixture from demethanization and then the gaseous hydrocarbon feed;

collecting the liquid olefins from said demethanization step and venting the hydrogen-methane mixture with reduced ethylene content from the process.

2. An apparatus for use in the process according to claim 3 comprising a first separation unit for isolating and recovering olefins from a pressurized gaseous hydrocarbon feedstock and a second unit including a single demethanizer for recovering residual olefins from the gaseous residue of the first separation unit;

said first unit comprising a plurality of stages, each stage comprising heat exchangers, coolers and liquid-gas separators wherein said feedstock in each stage is sequentially cooled to a lower temperature and the liquid condensate from the separator of said stage is delivered to the demethanizer in said second unit and the gas from said separation is fed to the next lower temperature stage; and said second unit comprising said demethanizer, a condenser for cooling the gaseous effluent from said demethanizer, a separator for separating the gases from the liquid condensate from said condenser into respective gas and liquid streams, and a first vortex tube and a second vortex tube, said first tube being fed by the gas stream separated from said condenser to form, from said vortex tube, a cold gas stream and a hot gas stream; the cold gas stream cooling said condenser and the hot gas stream feeding said second vortex tube wherein are formed a further cold gas stream and a further hot gas stream; said further cold gas stream being combined with the cold gas stream of said first vortex tube to cool said condenser; said further hot gas stream providing the countercurrent cooling for the successive stages of said first recovery unit; said demethanizer being provided with an effluent port for the separated olefins; and said first cooling stage of said first recovery unit being provided with venting means for residual hydrogen and methane.

* * * * *